(12) United States Patent
Naji et al.

(10) Patent No.: US 6,986,429 B2
(45) Date of Patent: Jan. 17, 2006

(54) ANTI-MICROBIAL POROUS COMPONENT FORMED OF A POLYMER MATERIAL GRAFTED WITH AMMONIUM UNITS

(75) Inventors: Mohammad Naji, Montpellier (FR); Bernard Pages, Montbazin (FR); Jacques Lacombes, Castelnau le Lez (FR)

(73) Assignee: Laboratoire Chauvin S.A., Montpellier (FR)

(*) Notice: Subject to any disclaimer, the term of this patent is extended or adjusted under 35 U.S.C. 154(b) by 182 days.

(21) Appl. No.: 10/258,832

(22) PCT Filed: Apr. 26, 2001

(86) PCT No.: PCT/FR01/01290

§ 371 (c)(1),
(2), (4) Date: Feb. 26, 2003

(87) PCT Pub. No.: WO01/82696

PCT Pub. Date: Nov. 8, 2001

(65) Prior Publication Data

US 2003/0159983 A1    Aug. 28, 2003

(30) Foreign Application Priority Data

Apr. 28, 2000    (FR) .................................. 00 05532

(51) Int. Cl.
*B01D 39/00* (2006.01)
*B01D 29/00* (2006.01)

(52) U.S. Cl. .................. 210/501; 210/488; 210/490; 210/500.1; 210/500.24; 210/500.41; 210/510.1; 424/400; 424/404; 264/628

(58) Field of Classification Search ................ 210/488, 210/490, 500.1, 500.24, 500.41, 501, 510.1; 424/400, 404; 264/628
See application file for complete search history.

(56) References Cited

U.S. PATENT DOCUMENTS

| 3,149,758 A | * | 9/1964 | Bush et al. ............ 222/189.09 |
| 4,335,141 A | * | 6/1982 | Grier et al. ................. 514/526 |
| 5,013,459 A | * | 5/1991 | Gettings et al. ............ 210/764 |

FOREIGN PATENT DOCUMENTS

| EP | 0478445 | 4/1992 |
| EP | 0558357 | 9/1993 |
| EP | 0952168 | 10/1999 |
| FR | 2686610 | 7/1993 |
| JP | 07323206 A | * 12/1995 |
| WO | WO 95/17152 | 6/1995 |

OTHER PUBLICATIONS

"Guidance for protecting Building Environments", NIOSH publication May 19, 2005 <<http://www.cdc.gov/niosh/docs/2003-136/2003-136c.html#partair>>.*
Database WPI; Section Ch, Week 199607; Derwent Publication Ltd., London, GB, AN 1996-064967; XP002157636 & JP07323206 A (Ebara Corp); Dec. 12, 1995.

* cited by examiner

*Primary Examiner*—W. L. Walker
*Assistant Examiner*—Krishnan S. Menon
(74) *Attorney, Agent, or Firm*—John E. Thomas

(57) ABSTRACT

The invention concerns an anti-microbial porous part based on a polymeric material grafted at the surface and in its volume with ammonium motifs with anti-microbial and/or bactericidal and/or fungicide activity, preferably benzalkonium. The invention is characterized in that it has a porosity sufficiently high to enable a liquid with compatible viscosity to pass through its structure and sufficiently low to trap contaminating germs within said structure.

14 Claims, 1 Drawing Sheet

Figures 1, 2:
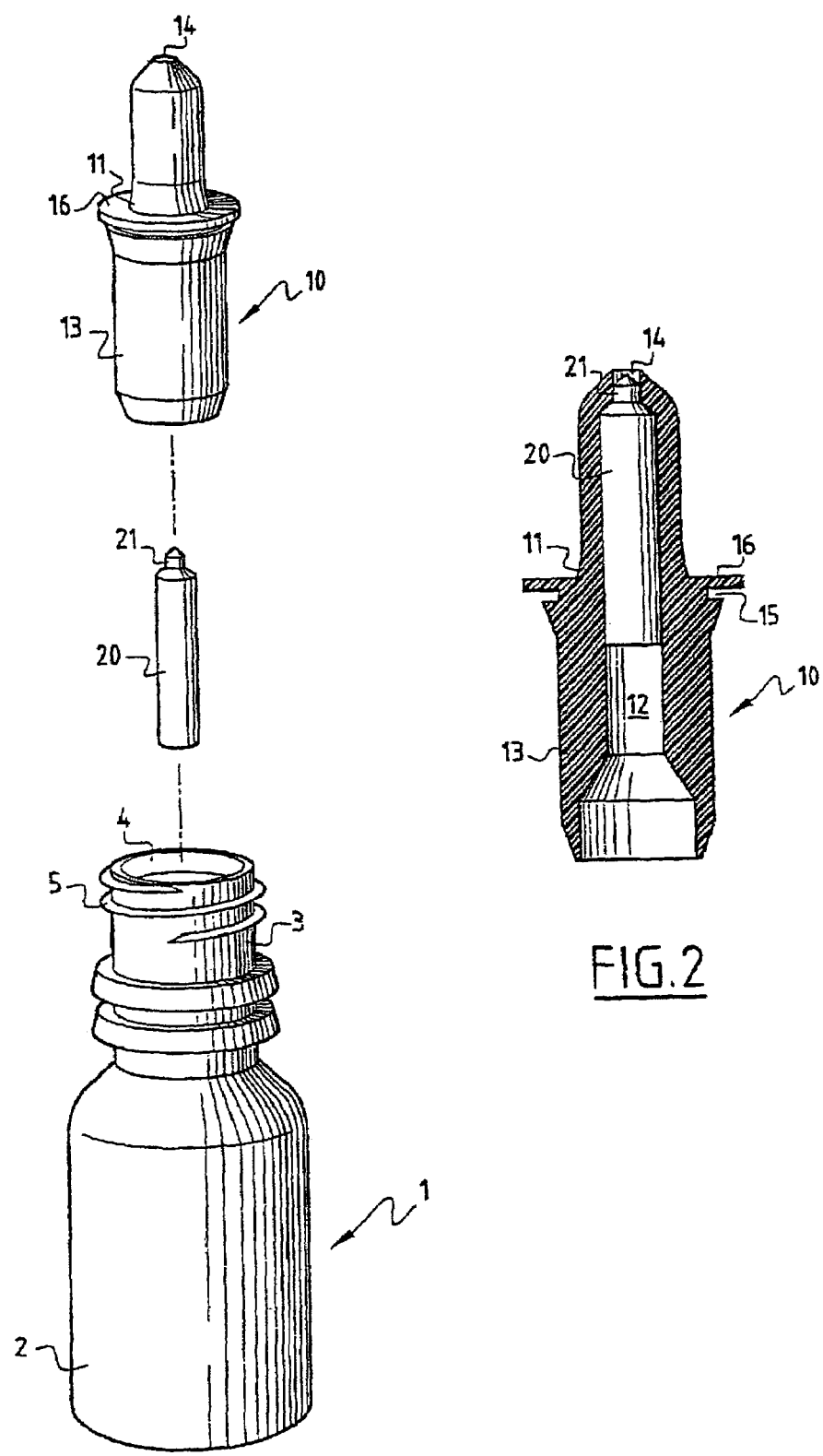

ANTI-MICROBIAL POROUS COMPONENT FORMED OF A POLYMER MATERIAL GRAFTED WITH AMMONIUM UNITS

The present invention relates to the field of packaging liquid solutions for which it is desired to ensure no microbial contamination. The fields for which the present invention is more particularly intended are those of pharmacy and especially that of ophthalmology.

In general, any liquid solution of the therapeutic and especially ophthalmic field is packaged in a device of bottle type adapted with a nozzle to distribute this solution. This nozzle is hermetically sealed until the time of use, so as to protect the packaged solution against any risk of contamination, in particular by microorganisms from the ambient atmosphere.

The problem posed and solved according to the present invention is directed toward ensuring that the packaged solution is protected after opening the bottle and during its period of use.

Two alternatives are currently available to assure the user of this antimicrobial protection.

The first option consists in offering him liquid solutions into which have been incorporated antimicrobial or bactericidal preserving agents. This type of solution has the advantage of being compatible with prolonged use of the packaged solution over time. On the other hand, these preserving agents may cause adverse side effects in the case of certain users.

The second option consists in formulating the solution in the form of single-use doses. The solutions thus packaged lack preserving agents, but, on the other hand, are incompatible with a prolonged use of more than 3 hours. The major drawback of this second type of packaging is thus threefold: cost, bulk of the packaging (for one month of treatment) and difficulty of installation and impossibility of reuse without the risk of contamination.

There is therefore currently a need for a novel packaging for a sterile liquid solution, which is compatible with prolonged use of this solution over time, but which does not require the incorporation into said solution of antimicrobial and/or bactericidal preserving agents.

New types of devices have been developed taking these considerations into account. However, they are not considered to be entirely satisfactory since they generally involve a new bottling concept which, for reasons of costs, has not been taken up by industrialists.

One object of the present invention is, specifically, to propose a solution that satisfies all the points discussed above.

A first aspect of the invention thus relates to a porous antimicrobial component based on polymer material grafted at the surface and in bulk with ammonium units with antimicrobial and/or bactericidal and/or fungicidal activity, characterized in that it has a porosity that is, on the one hand, high enough to allow the passage through its structure of a liquid of compatible viscosity, and, on the other hand, low enough to ensure that contaminant microorganisms are trapped within this structure.

The inventors have thus demonstrated that it is possible using such a porous component to satisfy all the requirements presented above.

The porous component according to the invention has the first advantage of being entirely compatible with the already-existing bottling devices. Given its size, it may be inserted easily into the distribution nozzle of bottles and provide at this level an effective barrier function between the solution packaged in the bottle receptacle and the end of the distribution nozzle exposed to the ambient atmosphere.

Owing to its chemical structure, which incorporates units with antimicrobial and/or bactericidal activity at the surface and in the bulk, it allows, by means of an effect of retention of the contaminant microorganisms, within its active surface, an effective isolation of these microorganisms with respect to the liquid solution, and then, by intimate contact between the material and the microorganisms, the reduction and elimination over time of such microorganisms.

Finally, its porous structure which has a deep-down internal network of tubules, allows the liquid solution to pass when it is administered.

The threefold objective mentioned previously is consequently achieved using the porous component according to the invention.

More specifically, the chemical structure of this porous component is derived from a polymer consisting of units of general formula I:

  (I)

in which Ar represents a chain of formula:

  (II)

or

  (III)

in which:
R represents a $C_2$–$C_{15}$ alkyl,
Ph is a phenyl unit, and
$X^-$ is chosen from the anions usually used in the field, which are pharmaceutically acceptable with chains of formula II being present in an amount that is sufficient to give the said material antimicrobial properties.

Representative of the ions featured by $X^-$, mention may be made more particularly of halides, for instance chloride, bromide or iodide, acetate, benzoate, carbonate, citrate, formate, gluconate, glycolate, hydroxide, lactate, malate, maleate, malonate, nitrate, phosphate, propionate, succinate, sulfate, tartrate and the like. According to one preferred variant of the invention, it is a chloride anion.

According to one preferred variant of the invention, the polymer is derived from a polystyrene, which is preferably non-crosslinked.

As regards the benzalkonium units of formula II, they preferably comprise as quaternary ammonium a dimethyltetradecylammonium group.

The content of units of benzalkonium type of formula II present on the polymer structure is liable to vary as a function especially of the nature of the polymer skeleton and of that of the substituents featured on the benzalkonium unit.

In point of fact, it is adjusted so as to achieve a compromise between the antimicrobial and/or antibacterial efficacy and the assurance, as regards the plastic material thus constituted, of a hydrophobicity which is compatible with the desired use. Specifically, an excessively high degree of grafting on the polymer can give it an excessively hydrophilic nature, which is reflected by the formation of a gel when the material comes into contact with an aqueous solution, this phenomenon not being compatible with the desired use.

When the polymer is made of a polystyrene skeleton, this compromise is advantageously achieved for a molar percentage of grafting from about 15% to 30%, and preferably of about 20%, i.e. a weight percentage of benzalkonium units of formula II of about 30% to 40%, and preferably of about 36%, of the mass of the grafted polymer thus obtained. Clearly, it is possible to lower this value as a function of the desired antimicrobial efficacy.

The polymer material is preferentially a polystyrene partially grafted with dimethyltetradecylammonium units and preferably grafted to a molar percentage of between 18% and 25%.

The polymer material may be obtained by reacting a polymer consisting of units

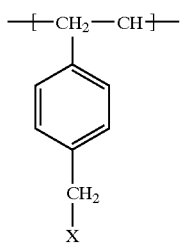

such as, preferably, a chloromethyl polystyrene, with an amine of formula $N(CH_3)_2(R)$ with X and R being as defined above, in a homogeneous medium, i.e. in a solubilized form, and in a molar ratio adjusted as a function of the desired degree of grafting.

According to one preferred preparation method, the polymer material is purified beforehand by dissolving it in an organic solvent such as dichloromethane and reprecipitating it by adding an alcohol such as methanol. The polymer thus recrystallized is collected by filtration. This step allows the removal from the polymer of low molecular weight compounds which, after the grafting reaction, are liable to be released into the aqueous medium.

The polymer thus purified and the amine defined above are dissolved in an organic medium such as acetone and kept stirring constantly for 24 hours at room temperature.

Preferably, the grafted amine is dimethyltetradecyl-amine and the molar percentage of grafting is in the region of 20%.

The material thus obtained is then isolated, preferably by precipitation by incorporating a solvent such as hexane into the reaction medium. This treatment not only allows the material to be purified, but also allows a powder of uniform particle size to be obtained. Adjusting the stirring conditions and the volumes of solvent used produces a product of perfectly controlled purity and particle size.

The antimicrobial and/or bactericidal and/or fungicidal activity of the material thus obtained was tested especially with respect to *Pseudomonas, Staphylococcus, Candida* and *Aspergillus* strains. This test forms the subject of Example 2 below.

The antimicrobial activity of the polymer material satisfies criteria A of the European Pharmacopoeia for 3 reference microorganisms (*Staphylococcus aureus, Pseudomonas aeruginosa* and *Candida albicans*) and criteria B for the fourth reference microorganism (*Aspergillus niger*), which is reputed to be relatively insensitive to quaternary ammoniums, even solubilized ones. With an initial contaminant load of 100 000 microorganisms (in 0.1 ml of microbial suspension) per 100 mg of material, these results obtained without stirring are entirely satisfactory and reproducible.

Similarly, the aqueous insolubility of the material and the absence of release of its constituent units (quaternary ammonium oligomers of low molecular weight) were demonstrated after 24 hours of contact with vigorous stirring between 2 grams of material and 100 ml of distilled water: the integrity of the solutions is thus ensured in the long term, since the contact between the porous component and the packaged solution is limited to the passage through the porous component during delivery.

The polymer material thus obtained is then fashioned as a single porous component. This fashioning may be performed according to various techniques familiar to those skilled in the art, such as, for example, the technique consisting in compacting the powder of the material defined above in the form of a sinter. In a mold of defined dimensions and under parameterized temperature and pressure conditions, the grains of material are softened to stick together so as thus to form a rigid plastic component. The interstices left free between the adhered grains of powder create a multidimensional network of tubules which give the component deep-down porosity.

After this fashioning, a material is thus obtained which is functionalized at the surface and in the bulk with units with antimicrobial activity, and which has a porosity that is sufficient to allow a solution of low viscosity to pass through the structure.

The deep-down porosity of the component defined above is conditioned firstly by the particle size homogeneity of the material and the mean grain size of the material, and secondly by the resistance of this same material to the temperature and pressure conditions used.

The porous component according to the invention is preferably in the form of a sinter whose deep-down porosity is between 5 and 30 microns, requiring a mean particle size of the material of between 30 and 350 microns and preferably between 80 and 125 microns.

A third aspect of the invention relates to the use of the porous component claimed in the distribution nozzle of a bottle for packaging a liquid solution.

The solutions concerned may be of very diverse nature. They may especially be solutions for food use (such as fruit juices or liquid yogurts), for medicinal use (such as drinkable solutions, syrups, ophthalmic solutions, nasal solutions or auricular solutions) or for dermatological use (such as bodily fluids or make-up-removing solutions).

In point of fact, the only selection criterion of this solution is linked to its viscosity. It must, of course, be compatible with the deep-down porosity of the porous component.

According to one preferred mode of the invention, the packaged solution is an ophthalmic solution.

The third aspect of the invention relates more particularly to a nozzle for distributing a liquid solution, of the type comprising a tube comprising an inner channel and fitted, at one of its ends, with an end piece for fitting into a bottle opening, and, at the other of a said ends, with an orifice for the dropwise delivery of the liquid solution, characterized in that the tube comprises in said inner channel a porous component as defined above.

As discussed previously, one of the advantages of the porous component claimed is that of being able to be adapted to any already-existing bottling system. Specifically,, it is possible to fashion, from the polymer material, porous components whose sizes are adjusted to the distribution nozzles of the bottles under consideration.

The examples and figures are given below for the purpose of nonlimiting illustration of the present invention.

FIGURES

FIG. 1 represents a diagrammatic view in exploded perspective of a bottle equipped with a liquid solution distribution nozzle, and FIG. 2 represents a diagrammatic view in axial cross section of this nozzle equipped with an antimicrobial porous component in accordance with the invention.

Shown in FIG. 1 is a bottle denoted as a whole by reference 1, which comprises a body 2 forming a reservoir intended to contain the liquid solution. The body 2 comprises at the top a neck 3 equipped with an opening 4 for mounting a nozzle for distributing said liquid solution contained in the body 2.

Moreover, the neck 3 is provided on its outer surface with a thread 5 to screw on a cap, not shown, intended to close the nozzle.

The nozzle denoted by the general reference 10 is formed of a tube 11 comprising an inner channel 12. This tube 11 is fitted, at one of its ends, with an end piece 13 for fitting into the opening 4 of the body 2 of the bottle 1 and, at the other of said ends, with an orifice 14 for dropwise delivery of the liquid solution contained in said bottle 1.

The tube 11 is also equipped externally with a groove 15 for snap-fitting onto a rim made in the orifice 4 of the body 2 and also with a stop flange ring 16 on the top edge of the neck 3 of the bottle 1.

The tube 11 comprises in the inner channel 12 an antimicrobial porous component 20.

Preferably, the porous component 20 comprises at one of its ends a tip 21 for penetrating into the orifice 14 for delivery of the liquid solution.

This porous component 20 has a porosity that is on the one hand high enough to allow the passage through its structure of a liquid of compatible viscosity, and on the other hand low enough to ensure that contaminant microorganisms are trapped within this structure.

These microorganisms are then, by contact activity, reduced and eliminated therein.

EXAMPLES

Example 1: Manufacture of an Antimicrobial Material

The chloromethyl polystyrene corresponds to the Aldrich reagent ref: 18,253-2/batch 00128 TQ.

The dimethyltetradecylamine corresponds to the Fluka reagent ref: 41653/batch 363679/1-22399.

The chloromethyl polystyrene (21 g) is dispersed in 2000 ml of methanol for 1 hour, recovered by filtration, dissolved in 130 ml of dichloromethane and then reprecipitated in 2000 ml of methanol. This step is repeated. The polymer thus purified is isolated by filtration after stirring for 1 hour 30 minutes, and then oven-dried at 40° C.

20 g of purified polymer are dissolved in 40 ml of acetone in a 2 liter round-bottomed flask with stirring, and 6.4 g of dimethyltetradecylamine are then incorporated. The mixture is stirred for 24 hours.

The grafted product is isolated by precipitation by gradually adding to the reaction medium with stirring 1500 ml of hexane. The mixture is stirred for 4 hours and the product obtained is then oven-dried at 40° C.

The product obtained is screened so as to obtain a particle size of between 80 and 125 microns.

25 grams of the product thus obtained are washed in 1000 ml of distilled water for 1 hour with stirring, and the final product is isolated by filtration and then oven-dried at 40° C. for 12 hours. 25 grams of the expected material are thus obtained.

The characterization of the material obtained was performed by proton Nuclear Magnetic Resonance in deuterated chloroform, Gel Permeation Chromatography, chloride assay and Differential Thermal Analysis: the results confirm the expected structure of the polymer.

The aqueous insolubility of the material was checked after 24 hours of contact under vigorous stirring between 2 grams of material and 100 ml of distilled water: no significant weight loss is detected on the material before and after treatment and the aqueous solution does not contain any soluble benzalkonium units. The UV, HPLC and GC monitoring of this same solution make it possible to conclude that the constituent low molecular weight compounds of the polymer are not released into the water to a dose of greater than 0.05 mg/liter, thus confirming that the antimicrobial activity of the material is a contact activity.

Example 2: Antimicrobial Efficacy of the Porous Component

In order to check the antimicrobial activity of the material defined above, the product is subjected to the antimicrobial conversion efficacy test of the European Pharmacopoeia.

The test microorganisms are *Pseudomonas aeruginosa, Staphylococcus aureus, Candida albicans* and *Aspergillus niger*.

For each test microorganism, 4 hemolysis tubes each containing 100 mg of material are inoculated with 100 000 microorganisms in 0.1 ml; homogenize and leave in contact without stirring.

At each prescribed interval (6 hours, 24 hours, 7 days, 14 days and 28 days of contact), the residual viable microorganisms were counted.

The results obtained are expressed relative to the initial count of the inoculum, in the form of a decimal logarithmic reduction.

The criteria of the European Pharmacopoeia are given in the following table:

| | | Parenteral and ophthalmic preparations | | | | |
|---|---|---|---|---|---|---|
| | | Logarithmic reduction | | | | |
| | | 6 hours | 24 hours | 7 days | 14 days | 28 days |
| Bacteria | CRITERIA A | 2 | 3 | — | — | NF* |
| | CRITERIA B | — | 1 | 3 | — | NI** |
| Fungi | CRITERIA A | — | — | 2 | — | NI** |
| | CRITERIA B | — | — | — | 1 | NI** |

*NF: not found
**NI: no increase

The results obtained on the material according to the invention described above are listed in the following table:

|  | Aspergillus niger ATCC 16 404 | Candida albicans ATCC 10 231 | Pseudomonas aeruginosa CIP 82 118 | Staphylococcus aureus CIP 4 83 |
|---|---|---|---|---|
| {Inoculum} in CFU/ml | $1.60 \times 10^6$ | $1.39 \times 10^6$ | $1.43 \times 10^6$ | $1.85 \times 10^6$ |
| Amount of CFU introduced in 0.1 ml | 160 000 | 139 000 | 143 000 | 185 000 |
| T 6 hours Amount of CFU counted in the dipping solution | — | — | 0 | 0 |
| Logarithmic reduction R | — | — | NF | NF |
| T 24 hours Amount of CFU counted in the dipping solution | — | — | 0 | 0 |
| Logarithmic reduction R | — | — | NF | NF |
| T 7 days Amount of CFU counted in the dipping solution | 95 000 | 0 | 0 | 0 |
| Logarithmic reduction R | 0.23 | NF | NF | NF |
| T 14 days Amount of CFU counted in the dipping solution | 2 576 | 0 | — | — |
| Logarithmic reduction R | 1.79 | NF | — | — |
| T 28 days Amount of CFU counted in the dipping solution | 0 | 0 | 0 | 0 |
| Logarithmic reduction R | NF | NF | NF | NF |
| Conclusion: criterion obtained | B | A | A | A |

NF = not found

The antimicrobial activity of the polymer material satisfies criteria A of the European Pharmacopoeia for *Staphylococcus aureus, Pseudomonoas aeruginosa* and *Candida albicans* (the microorganisms being entirely eliminated after 6 hours for the two bacteria and 7 days for the yeast, respectively) and criteria B for *Aspergillus niger* (the mold being totally eliminated after 28 days).

What is claimed is:

1. A porous antimicrobial component formed of a polymer material grafted at its surface and in its bulk with ammonium units, said ammonium units having at least one of antimicrobial activity, bactericidal activity and fungicidal activity, said polymer material derived from a polymer comprising units of formula (I)

—[CH$_2$—CH(Ar)]      (I)

in which Ar represents a chain of formula:

-Ph-CH$_2$—N$^{\oplus}$(CH$_3$)$_2$R,X$^{\ominus}$      (II)

or

-Ph-CH$_2$—X      (III)

in which:
R represents a C$_2$–C$_{15}$ alkyl,
Ph is a phenyl unit, and
the ion X$^-$ is a pharmaceutically acceptable anion, with chains of formula II being present in an amount that is sufficient to give said material antimicrobial properties, and wherein the polymer is a polystyrene partially grafted with dimethyltetradecylamine units.

2. The porous component according to claim 1, wherein the polystyrene is grafted to a molar percentage of 15% to 30% of benzalkonium units.

3. The porous component according to claim 1, which is in the form of a sinter.

4. A process for preparing a porous antimicrobial component, wherein the porous component is formed of a polymer material grafted at its surface and in its bulk with ammonium units, said ammonium units having at least one of antimicrobial activity, bactericidal activity and fungicidal activity, said polymer material derived from a polymer comprising units of formula (I)

—[CH$_2$—CH(Ar)]      (I)

in which Ar represents a chain of formula:

-Ph-CH$_2$—N$^{\oplus}$(CH$_3$)$_2$R,X$^{\ominus}$      (II)

or

-Ph-CH$_2$—X      (III)

in which:
R represents a C$_2$–C$_{15}$ alkyl,
Ph is a phenyl unit and
the ion X$^-$ is a pharmaceutically acceptable anion, with chains of formula II being present in an amount that is sufficient to give said material antimicrobial properties, said process comprising: reacting a polymer comprising units:

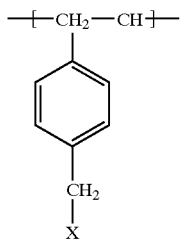

with an amine of formula $N(CH_3)_2(R)$, with X and R being as defined above, at a desired a molar ratio, and recovering the reaction product in the form of a powder and forming the powder into said porous component.

5. The process according to claim 4, wherein the starting polymer is a chloromethyl polystyrene.

6. The process according to claim 4, wherein the amine reactant is dimethyltetradecylamine.

7. The process according to claim 4, wherein the powder is formed into the porous component by sintering.

8. A bottle for packaging a liquid solution, comprising a distribution nozzle that includes a porous component as claimed in claim 1.

9. The bottle of claim 8, wherein the liquid solution is a solution for food, medicinal or dermatological use.

10. The bottle according to claim 8, wherein the bottle is for packaging an ophthalmic solution.

11. A liquid solution distribution nozzle comprising a tube that comprises an inner channel and equipped, on one of its ends, with an end piece for fitting into a bottle opening and equipped, at an opposed end, with an orifice for dropwise delivery of the liquid solution, wherein the tube comprises in said inner channel the porous component as claimed in claim 1.

12. The porous component of claim 1, wherein the polystyrene is grafted with 30% to 40% benzalkonium units based on weight percent of the grafted polymer.

13. The porous component of claim 1, having a porosity between 5 and 30 microns.

14. The method of claim 4, wherein the porous component has a porosity between 5 and 30 microns.

* * * * *

UNITED STATES PATENT AND TRADEMARK OFFICE
CERTIFICATE OF CORRECTION

PATENT NO.        : 6,986,429 B2                                                Page 1 of 1
APPLICATION NO.   : 10/258832
DATED             : January 17, 2006
INVENTOR(S)       : Mohammad Naji et al.

It is certified that error appears in the above-identified patent and that said Letters Patent is hereby corrected as shown below:

Col. 7, line 54

Replace "—Ph—$CH_2$—$N^{\oplus}(CH_3)_2 R, X^{\ominus tm}$"

With -- —Ph—$CH_2$—$N^{\oplus}(CH_3)_2 R, X^{\ominus}$ --.

Signed and Sealed this

Eighth Day of May, 2007

JON W. DUDAS
*Director of the United States Patent and Trademark Office*